United States Patent [19]

Dappen et al.

[11] Patent Number: 5,436,249

[45] Date of Patent: * Jul. 25, 1995

[54] OPIOID AGONIST COMPOUNDS

[75] Inventors: Michael S. Dappen, Daly City, Calif.; Barnett S. Pitzele, Skokie; Michael F. Rafferty, Buffalo Grove, both of Ill.

[73] Assignee: G. D. Searle & Co., Chicago, Ill.

[*] Notice: The portion of the term of this patent subsequent to Jul. 6, 2010 has been disclaimed.

[21] Appl. No.: 243,661

[22] Filed: May 16, 1994

Related U.S. Application Data

[63] Continuation of Ser. No. 21,694, Feb. 24, 1993, Pat. No. 5,354,863, which is a continuation-in-part of Ser. No. 823,221, Jan. 21, 1992, Pat. No. 5,225,417.

[51] Int. Cl.⁶ .................. A61K 31/44; C07D 491/12
[52] U.S. Cl. ......................... 514/279; 546/35
[58] Field of Search ..................... 546/35; 514/279

[56] References Cited

U.S. PATENT DOCUMENTS

| | | | |
|---|---|---|---|
| 4,816,586 | 3/1989 | Portoghese | 544/340 |
| 5,225,417 | 7/1993 | Dappen et al. | 514/279 |

OTHER PUBLICATIONS

"Design of Peptidomimetic Delta Opiod Receptor Antagonists Using the Message Address Concept," J. Med. Chem. 33, pp. 1714–1720, Jan., 1990, U.S.A.

"Application of the Message Address Concept in the Design of Highly Potent and Selective Non–Peptide S Opiod Receptor Antagonists," J. Med. Chem. 31, No. 2, pp. 281–282, Jan., 1988, U.S.A.

*Primary Examiner*—Cecilia Tsang
*Attorney, Agent, or Firm*—Roberta L. Hastreiter; Roger A. Williams

[57] ABSTRACT

The present invention provides novel substituted opioid analgesic compounds of Formula I:

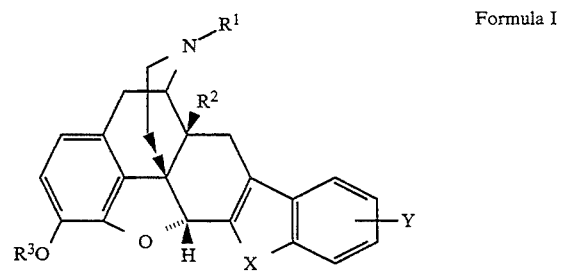

Formula I which are opioid agonists, and which are useful as analgesic agents for the treatment of pain, pharmaceutical compositions comprising a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

10 Claims, No Drawings

OPIOID AGONIST COMPOUNDS

This application is a continuation application Ser. No. 08/021,694, filed on Feb. 24, 1993, now U.S. Pat. No. 5,354,863 which is a continuation-in-part application of U.S. Ser. No. 07/823,221, filed on Jan. 21, 1992, which is now issued U.S. Pat. No. 5,225,417.

BACKGROUND OF THE INVENTION (1) Field of the Invention

The present invention generally relates to compounds having pharmacological activity which are useful as pharmacological agents and, more particularly, as analgesic agents for the treatment of pain, to pharmaceutical compositions containing one or more of these compounds, and to methods of treatment employing these compounds. More particularly, the present invention concerns novel opioid analgesic compounds, pharmaceutical compositions containing one or more of these compounds in combination with a pharmaceutically-acceptable carrier, and methods of treating pain employing these compounds.

Analgesic compounds are agents which alleviate pain without causing a loss of consciousness and, thus, which are useful for treating pain.

The major classes of analgesic compounds include narcotic analgesics, or opiates, compounds which alleviate pain and induce sleep, and analgesic-antipyretic compounds, compounds which alleviate pain and reduce fever, such as salicylates.

Although the efficacy of opiates in relieving pain is well established, the associated addiction liability of opiates is a distinct disadvantage of these compounds.

While salicylate and salicylate-like agents (non-steroidal antiinflammatory agents or NSAIDS) are also efficacious in relieving pain, they often exhibit undesirable side effects, such as gastrointestinal irritation, as with aspirin, allergic response, as with aspirin, and/or liver toxicity with extended use, as with acetaminophen.

The compounds of the present invention are novel opioid agonist analgesic compounds of comparable potency to morphine. The compounds have the potential for reduced side effects such as abuse potential, addiction liability, tolerance, respiratory depression and/or constipation, as compared to other agonists.

(2) Description of the Related Art

U.S. Pat. No. 4,816,586, issued on Mar. 28, 1989, discloses delta opioid receptor antagonists of the formula:

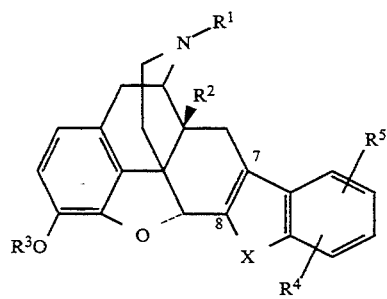

OR

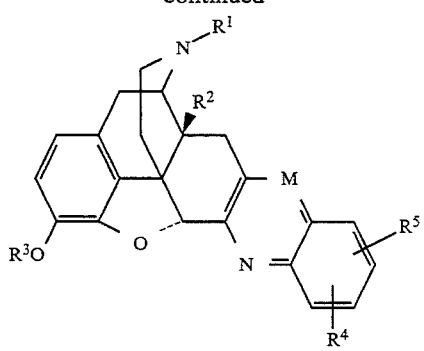

which are described as being useful for blocking delta-opioid receptors in mammalian tissue by contacting the receptors with one of the delta-opioid antagonists of the noted formulae. The antagonists are suggested for use as pharmacologic and biochemical probes of opioid receptor structure and function and for use clinically, i.e., to counteract life-threatening shock.

The document described hereinabove discloses compounds which are structurally different from the compounds of the present invention. Thus, the compounds of the present invention are structurally distinct from that which has been described in the art.

SUMMARY OF THE INVENTION The present invention provides compounds having a structure of Formula I:

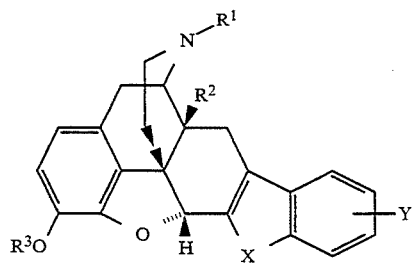

or a pharmaceutically-acceptable salt thereof, wherein:
$R^1$ represents hydrogen, $C_1$–$C_6$ alkyl, $C_3$–$C_6$ alkenyl, aryl, —CN,

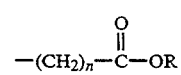

or —A–B, wherein n is an integer of from 1 to 5, and wherein A represents alkylene and B represents aryl or arylalkylhydroxy;

R represents —H, —$C_1$–$C_5$ alkyl, —$C_3$–$C_6$ alkenyl or alkylaryl;

$R^2$ represents halogen, —$NO_2$, —$NR^7R^7$, —$SR^7$ or —$OR^4$;

$R^3$ represents hydrogen, $C_1$–$C_6$ alkyl, aryl, aralkyl or

$R^4$ represents hydrogen, $C_1$–$C_5$ alkyl,

aryl or alkylaryl;

X represents $-NR^6$, O or S;

$R^5$ represents hydrogen, $C_1$-$C_5$ alkyl, $C_1$-$C_5$ alkylaryl, $C_3$-$C_6$ alkenyl, $C_1$-$C_5$ alkoxy or arylalkoxy;

$R^6$ represents hydrogen or $C_1$-$C_6$ alkyl;

$R^7$ represents hydrogen, $C_1$-$C_6$ alkyl or

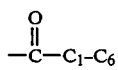

alkyl; and

Y represents hydrogen,

$-CN$, $-CF_3$, I or $-SR^6$.

The present invention also provides pharmaceutical compositions which are pharmaceutically acceptable and which comprise a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

DETAILED DESCRIPTION OF THE INVENTION

(1) Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The abbreviation "Ac" and the term "acetyl" as used herein mean the group

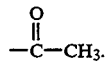

The abbreviations "AcOH" and "HOAc" as used herein mean

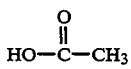

and acetic acid.

The term "alkenyl" as used herein means a hydrocarbon radical having from one to ten carbon atoms ($C_1$-$C_{10}$), within which includes from one to five carbon atoms ($C_1$-$C_5$), and further within which includes from one to three carbon atoms ($C_1$-$C_3$), which can be a straight or branched chain, and which contains from one to two $-C=C-$ groups.

The term "alkoxy" as used herein means an alkyl radical, as defined below, having an oxygen atom attached thereto, such as $-O-C_1-C_5$ alkyl ($C_1$-$C_5$ alkoxy). Representative alkoxy groups include methoxy, ethoxy, n-propoxy, tert-butoxy and the like.

The term "alkyl" as used herein means a saturated hydrocarbon radical having from one to ten carbon atoms ($C_1$-$C_{10}$), within which includes from one to six carbon atoms ($C_1$-$C_6$), and further within which includes from one to three carbon atoms ($C_1$-$C_3$), which can be a straight or branched chain. Representative of such radicals are methyl, ethyl, n-propyl, isopropyl, n-butyl, sec-butyl, isobutyl, tert-butyl, 2-ethylhexyl and the like.

The term "alkylaryl" as used herein means an alkyl radical, as defined above, having an aryl group, as defined below, attached thereto.

The term "alkylhydroxy" as used herein means an alkyl radical, as defined above, having a hydroxy group attached thereto, such as $-C_1-C_5-OH$.

The term "alkylene" as used herein means a straight or branched saturated hydrocarbon chain spacer arm.

The term "analgesia" as used herein means the reduction, or absence, of sensibility to pain, designating particularly the relief of pain without loss of consciousness.

The term "animal" as used herein includes mammals and non-mammals, and further includes humans and non-human animals.

The term "aryl" as used herein means 5- and 6-membered single-ring aromatic radicals which may include from zero to two heteroatoms in the ring, selected from oxygen and, nitrogen. Representative aryls include phenyl, thienyl, furanyl, pyridinyl, imidazolyl, thiazolyl, pyrimidinyl, pyrazinyl, pyridazinyl, (is)oxazolyl, triazolyl, tetrazolyl, pyrrolyl, pyridinyl-N-oxide and the like.

The term "aralkyl" as used herein means an aryl group, as defined above, having an alkyl group, as defined above, attached thereto, for example phenylethyl and N-methylpyrrolyl.

The term "arylalkylhydroxy" as used herein means an aryl group, as defined above, which has an alkylhydroxy group, as defined above, attached thereto.

The abbreviation "Boc" as used herein means t-butyloxycarbonyl.

The abbreviation "Bzl" and the term "benzyl" as used herein mean $C_6H_5CH_2-$.

The abbreviation "ca." as used herein means approximately.

The abbreviation "calcd" as used herein means calculated.

The term "carbonyl" as used herein means

The term "carboxyl" as used herein means

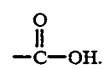

The abbreviation "cmpd" as used herein means compound.

The term "composition" as used herein means a product which results from the combining of more than one ingredient.

The abbreviation "DMF" as used herein means dimethylformamide.

The phrase "EC$_{50}$ dose" as used herein means that dose of a compound or drug which is necessary to elicit a 50% maximal biological response and, thus, which is necessary to elicit a 50% reduction in the contractions of guinea pig ileum segments in a prostaglandin antagonism assay.

The phrase "ED$_{50}$ dose" as used herein means that dose of a compound or drug which produced a defined biological effect, such as producing analgesia, in 50% of the animals to which the compound or drug was administered.

The abbreviation "equiv" as used herein means equivalent.

The abbreviation "Et" as used herein means ethyl (—CH$_2$CH$_3$).

The abbreviation "EtOH" as used herein means ethanol (CH$_3$CH$_2$OH).

The term "flash chromatography" as used herein is described in J. Org. Chem. 1978, 43,2923.

The abbreviation "$^1$H NMR" as used herein means Proton Nuclear Magnetic Resonance.

The term "halo" or "halogen" as used herein means chlorine (Cl), bromine (Br), fluorine (F) and/or iodine (I).

The term "heteroatom" as used herein means an atom of any element other than carbon or hydrogen.

The abbreviation "i.g." and the term "intragastrically" as used herein mean that a compound or drug was administered into the stomach.

The abbreviation "Me" as used herein means methyl (—CH$_3$).

The abbreviation "MeI" as used herein means methyl iodide.

The abbreviation "MeOH" as used herein means methanol (CH$_3$OH).

The abbreviation "NC" as used herein means not calculated.

The phrase "N-protecting group" or "N-protected" as used herein means those groups intended to protect the N-terminus of an amino acid or peptide, to protect an amino group against undesirable reactions during synthetic procedures and includes, but is not limited to, sulfonyl, acyl, acetyl, pivaloyl, t-butyloxycarbonyl (Boc), benzyloxycarbonyl (Cbz), benzoyl and an L- or D-aminoacyl residue, which may itself be N-protected similarly.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The abbreviation "Ph" and the term "phenyl" as used herein mean the group C$_6$H$_5$—, derived from benzene.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with a suitable base. Representative salts include the hydrochloride, hydrobromide, sulfate, bisulfate, acetate, valerate, oleate, palmitate, stearate, laurate, benzoate, lactate, phosphate, tosylate, citrate, maleate, fumarate, succinate, tartrate, napsylate, clavulanate and the like salts and alkali metal salts such as sodium and potassium and alkaline earth salts, such as calcium and magnesium.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The abbreviation "pyr" as used herein means pyridine.

The abbreviation "s.c." as used herein means that a compound or drug was administered subcutaneously.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

The abbreviation "THF" as used herein means tetrahydrofuran.

The phrases "title compound, " "title product," "title peptide" and "title material" as used herein mean that compound, product, peptide or material whose chemical name is given, and whose structure is shown, in the particular example, or subpart thereof, referred to. If no particular example, or subpart thereof, is referred to, it means that compound, product, peptide or material whose chemical name is given, and whose structure is shown, in the particular example, or subpart thereof, in which it appears.

(2) Description of Invention

In one aspect, the present invention provides compounds comprising a structure of Formula I, as described above, and pharmaceutically-acceptable-salts, esters and amides thereof.

The compounds of the present invention comprise a class of substituted morphinan compounds which compounds have been shown to exhibit activity as opioid agonists.

Specific compounds within the scope of the invention include, but are not limited to, the compounds discussed in the examples presented below, as well as their pharmaceutically-acceptable salts, esters, and amides.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of the present invention may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, S. M. Berge et al., "Pharmaceutical Salts, ." $J\ Pharm\ Sci.,$ 66:1-19 (977).)

In other cases, the compounds of the invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Berge et al., "Pharmaceutical Salts," supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. The pharmaceutical compositions of the invention may be specially formulated for oral administration in solid or liquid form, for parenteral injection, or for rectal or vaginal administration.

In yet a further aspect, the present invention provides a method for eliminating or ameliorating pain in an animal, and methods for treating central nervous disorders, including convulsions and ischemia, and asthma, enuresis, arrhythmia, diarrhea, dysmenorrhea and osteoporosis in an animal, comprising administering a therapeutically-effective amount of a compound of Formula I, as described hereinabove, to the animal.

The most preferred embodiment of the present invention is the compound described in Example 9 below.

(3) Utility

Compounds of the present invention exhibit activity as opioid agonist analgesics.

Compounds within the present invention, and the pharmaceutical compositions comprising one or more of these compounds, are useful as analgesic agents for the elimination or amelioration of pain in animals.

(4) Methods of Preparation

In general, the compounds of the present invention may be prepared by the methods illustrated in the following general reaction schemes, or by modifications thereof, using readily-available starting materials, reagents and conventional synthesis procedures. Unless otherwise specified, the various substituents of the compounds and materials present in the general reaction schemes are defined in the same manner as they are defined above in Formula I.

If a particular enantiomer of a compound of the present invention is desired, it may be prepared by chiral synthesis, by derivation with a chiral auxiliary, where the resulting diastereomeric mixture is separated and the auxiliary group cleaved to provide the pure desired enantiomers or by synthetic modification of a chiral enantiomerically enriched material. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The compounds of this invention may be prepared by the methods illustrated in one or more of the three general reaction schemes presented hereinbelow.

General Reaction Scheme No. 1 depicts the cyclization reaction to form the indole or benzofuran ring system. The known morphinoid ketones ($R^1$=hydrogen, $C_1$-$C_6$ alkyl, $C_3$-$C_6$ alkenyl, aryl, —CH,

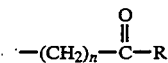

or —A—B, wherein n is an integer of from 1 to 5, wherein R is —OH, —O-$C_1$-$C_5$ alkyl, —O-$C_3$-$C_6$ alkenyl or alkylaryl and wherein A is alkylene and B is aryl or arylalkylhydroxy; $R^2$=halogen, —$NO_2$, —$NR^7R^7$, $SR^7$ or $OR^4$, wherein $R^7$ is hydrogen, $C_1$-$C_6$ alkyl or

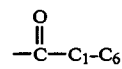

alkyl and wherein $R^4$ is hydrogen, $C_1$–$C_5$ alkyl,

aryl or alkylaryl; and $R^3$ = hydrogen, $C_1$–$C_6$ alkyl, aryl, aralkyl or

wherein $R^5$ is hydrogen, $C_1$–$C_5$ alkyl, $C_1$–$C_5$ alkylaryl, $C_3$–$C_6$ alkenyl, $C_1$–$C_5$ alkoxy or arylalkoxy) were treated with a substituted or unsubstituted phenyl hydrazine (X=NH; and Y=H) or a substituted or unsubstituted O-phenyl hydroxylamine (X=O, S or $NR^6$ wherein $R^6$ is $C_1$–$C_6$ alkyl; and

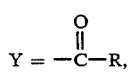

—CN, —$CF_3$, I or $SR^6$, wherein R is as defined above, and wherein $R^6$ is hydrogen or $C_1$–$C_6$ alkyl) using an appropriate solvent and acid catalyst to give the desired products.

General Reaction Scheme No. 2 shows the reaction sequence used to effect the removal of the methyl group on the nitrogen and subsequent replacement with the various $R^1$ groups discussed above for General Reaction Scheme No. 1. In General Reaction Scheme No 2, $R^2$ is —OH, $R^3$ and Y are each hydrogen and X is oxygen. Thus, the C-3 and C-14 hydroxyl groups are protected by treatment with acetic anhydride and pyridine to give the diacetoxy compound. Treatment of this compound with cyanogen bromide in chloroform yields the N-cyano compound No. 1. Treatment of compound No. 1 with aqueous sodium hydroxide in ethanol gives compound No. 2. Three methods were used to add various $R^1$ groups to give novel compounds. Method a involves alkylation in dimethylformamide using a halo-substituted $R^1$. Compound Nos. 3, 4, 8, and 16 were prepared in this manner. Method b involves the reaction of compound No. 2 with a carboxylic acid chloride to form a carboxylic acid amide. Reduction with lithium tetrahydroaluminate yields novel $R^1$=alkyl or aryl-substituted morphinoids. Method c involves reductive amination with compound No. 2 using sodium cyanoborohydide and an appropriate aldeydyde. Compounds Nos. 7, 13, 14, and 15 were prepared via method c. All other contemplated $R^1$ substitutions can be prepared via these three methods.

General Reaction Scheme No. 3 depicts the general method to install various $R^4$ substitutions into the compounds of the invention. In General Reaction Scheme No 3, $R^1$ X and Y are each as defined above for General Reaction Scheme No 1, $R^2$ is —$OR^4$, wherein R4 is as defined above for General Reaction Scheme No. 1, and $R^3$ is hydrogen. Thus, the C-3 hydroxyl was selectively methylated using potassium hydride and iodomethane to give the C-3 O-methyl compound. Further treatment with potassium hydride and an appropriate organohalide installs the $R^4$ group on the C-14 hydroxyl. Demethylation via standard conditions, such as boron tribromide or sodium ethanethiolate in methylene chloride, yields novel compounds with a C-14 -$OR^4$ substitution.

Where specific compounds are referred to hereinabove, for example, compound No. 1, the compounds referred to are those compounds which are shown and described in the examples presented hereinbelow.

GENERAL REACTION SCHEME NO. 1

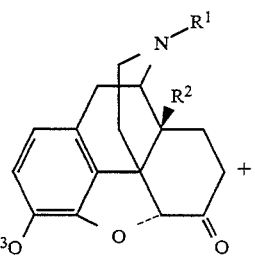

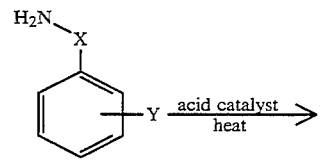

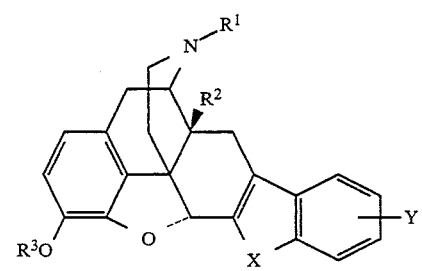

GENERAL REACTION SCHEME NO. 2

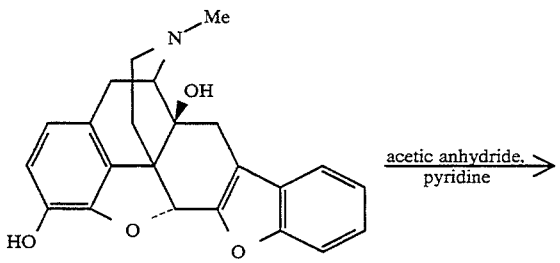

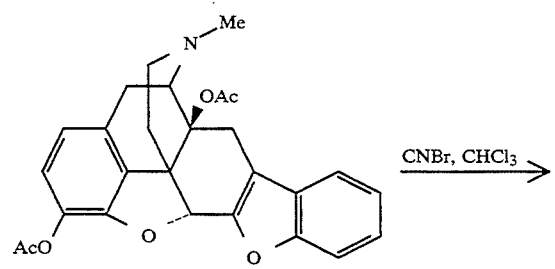

GENERAL REACTION SCHEME NO. 2 -continued

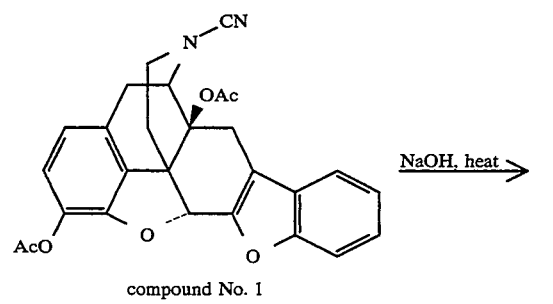

compound No. 1

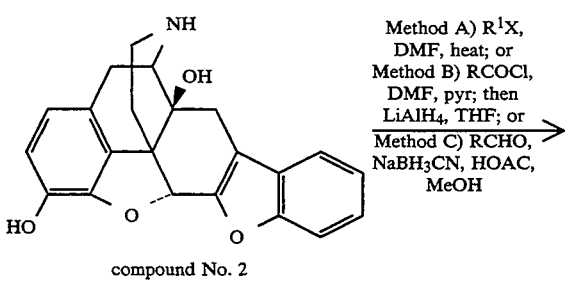

compound No. 2

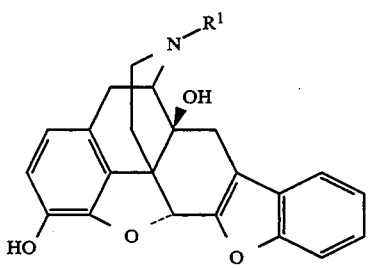

GENERAL REACTION SCHEME NO. 3

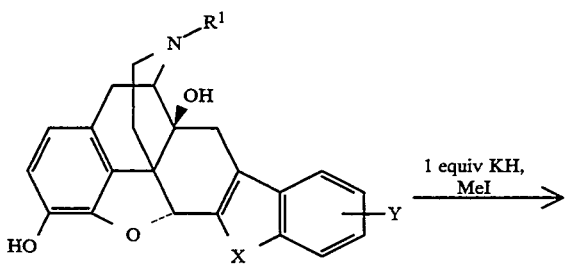

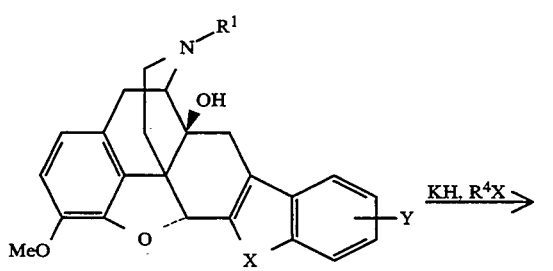

GENERAL REACTION SCHEME NO. 3 -continued

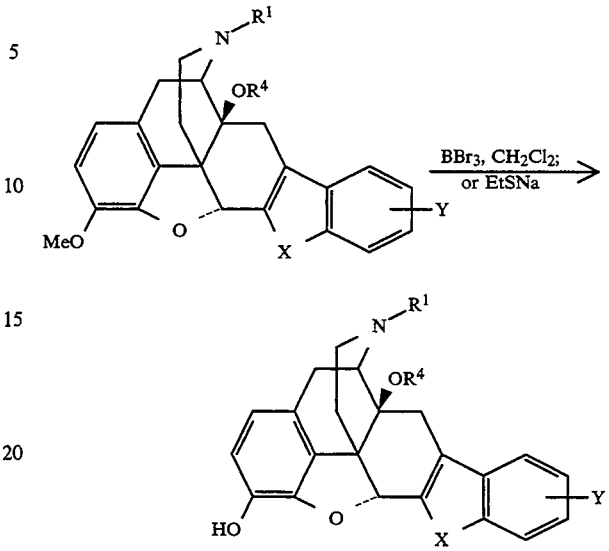

While the various aspects of the present invention are described herein with some particularity, those of skill in the art will recognize numerous modifications and variations which remain within the spirit of the invention. These modifications and variations are within the scope of the invention as described and claimed herein.

(5) Examples

The following examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

In the examples, all parts are by weight unless otherwise indicated.

All starting materials and equipment employed in the examples are commercially available. Sources for these materials include Sigma Chemical Co. (St. Louis, Mo.), Aldrich Chemical Co. (Milwaukee, Wis.), Lancaster Synthesis (Windham, N.H.), Fisher Scientific (Pittsburgh, Pa.), Boehringer Mannheim Biochemicals (Indianapolis, Ind.), Fluka Chemical Corp. (Ronkonkoma, N.Y.), Mallinckrodt Chemical Co. (St. Louis, Mo.), and Chemical Dynamics Corp. (South Plainfield, N.J.). Most of the starting materials were obtained from Aldrich Chemical Co. (Milwaukee, Wis.) or Mallinckrodt Chemical Co. (St. Louis, Mo.).

All patents and publications referred to in the examples, and throughout the specification, are hereby incorporated herein by reference, without admission that such is prior art.

| Cmpd No. | Structure | Molecular Formula | Microanalysis | | Optical $[\alpha]_D$ |
|---|---|---|---|---|---|
| | | | Calcd | Found | |
| 1 | 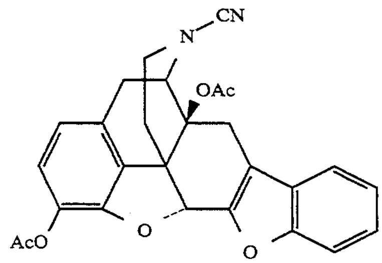 | $C_{27}H_{22}N_2O_6$ | C 68.93<br>H 4.71<br>N 5.95 | 68.81<br>4.81<br>5.44 | −387.7° |
| 2 | 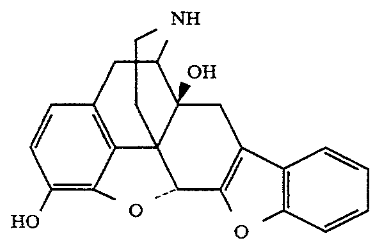 | $C_{22}H_{19}NO_4$<br>+ 0.3 H$_2$O | C 72.04<br>H 5.39<br>N 3.82 | 71.95<br>5.55<br>3.79 | NC |
| 3 | 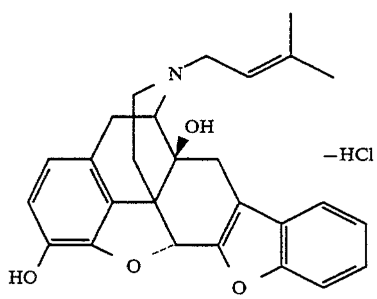 | $C_{27}H_{28}NO_4Cl$ + 0.4 H$_2$O | C 68.53<br>H 6.14<br>N 2.96<br>Cl 7.49 | 68.58<br>5.97<br>2.91<br>7.45 | −370.8° |
| 4 | 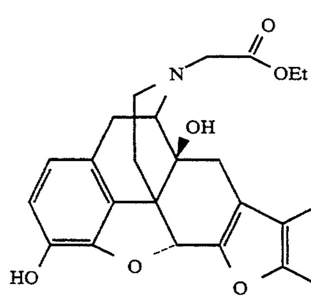 | $C_{26}H_{25}NO_6$ + 0.8 HCl + 0.2 H$_2$O | C 65.02<br>H 5.50<br>N 2.92<br>Cl 5.91 | 65.03<br>5.39<br>2.90<br>5.62 | −390.6° |
| 5 | 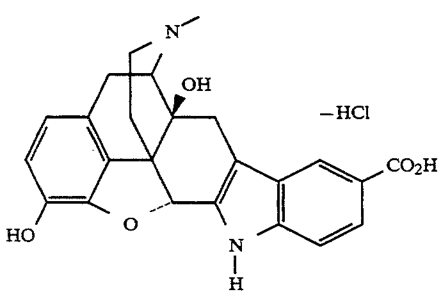 | $C_{24}H_{23}N_2O_5Cl$ + 1.0 H$_2$O | C 60.95<br>H 5.33<br>N 5.92<br>Cl 7.50 | 61.18<br>5.09<br>5.99<br>8.08 | −251.6° |

-continued

| Cmpd No. | Structure | Molecular Formula | Microanalysis | | | Optical $[\alpha]_D$ |
|---|---|---|---|---|---|---|
| | | | | Calcd | Found | |
| 6 | 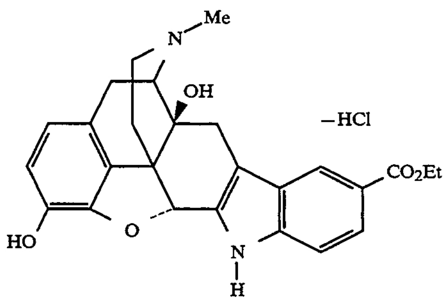 | $C_{26}H_{28}N_2O_5Cl$ + 0.5 $H_2O$ | C<br>H<br>N | 63.47<br>5.74<br>5.69 | 63.46<br>5.79<br>5.61 | −330.8° |
| 7 | 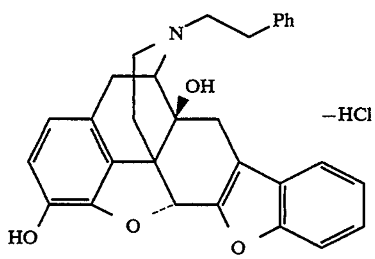 | $C_{30}H_{28}NO_4Cl$ + 0.2 HCl + 0.2 EtOH | C<br>H<br>N<br>Cl | 70.42<br>5.72<br>2.72<br>8.21 | 70.59<br>5.63<br>2.70<br>8.00 | −339.4° |
| 8 | 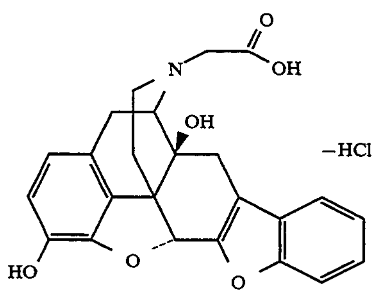 | $C_{24}H_{21}NO_6$ + 0.9 HCl + 1.0 $H_2O$ | C<br>H<br>N<br>Cl | 61.30<br>5.12<br>2.98<br>6.79 | 61.11<br>4.93<br>3.29<br>6.40 | −372.5° |
| 9 | 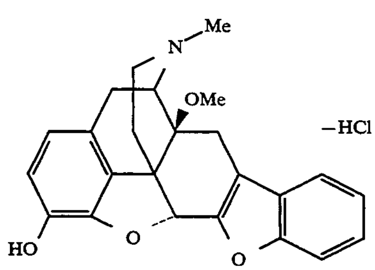 | $C_{24}H_{24}NO_4Cl$ + 1.3 $H_2O$ | C<br>H<br>N<br>Cl | 64.15<br>5.97<br>3.12<br>7.89 | 63.97<br>5.57<br>3.06<br>7.53 | −376.6° |
| 10 | 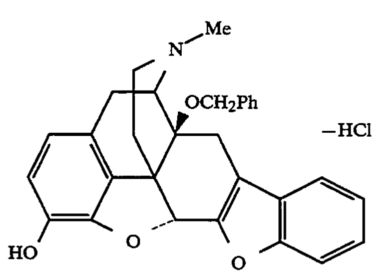 | $C_{30}H_{28}NO_4Cl$ + 1.1 $H_2O$ | C<br>H<br>N<br>Cl | 69.05<br>5.83<br>2.68<br>6.79 | 68.84<br>5.53<br>2.64<br>6.94 | −346.0° |

-continued

| Cmpd No. | Structure | Molecular Formula | Microanalysis Calcd | Found | Optical $[\alpha]_D$ |
|---|---|---|---|---|---|
| 11 | 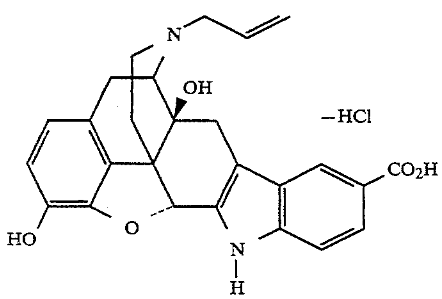 | $C_{26}H_{24}N_2O_5$ + 0.88 HCl + 1.75 H$_2$O | C 61.48<br>H 5.63<br>N 5.52<br>Cl 6.11 | 61.56<br>5.23<br>5.47<br>5.75 | −213.2° |
| 12 | 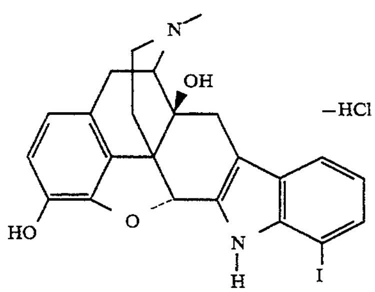 | $C_{23}H_{22}N_2O_3ClI$ + 0.2 H$_2$O | C 51.12<br>H 4.18<br>N 5.18<br>Cl 6.56 | 50.73<br>4.20<br>5.12<br>6.73 | NC |
| 13 | 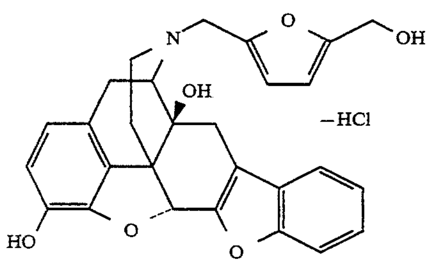 | $C_{28}H_{26}NO_6Cl$ + 1.5 H$_2$O | C 62.86<br>H 5.46<br>N 2.62<br>Cl 6.63 | 62.93<br>5.09<br>2.64<br>6.85 | NC |
| 14 | 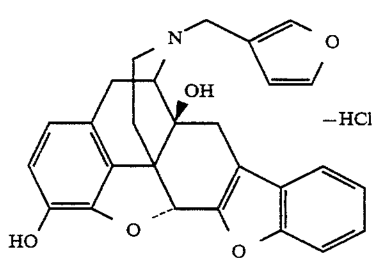 | $C_{27}H_{27}NO_6Cl$ + 1.5 H$_2$O | C 63.09<br>H 5.43<br>N 2.72<br>Cl 7.59 | 63.00<br>4.74<br>2.69<br>7.73 | NC |
| 15 | 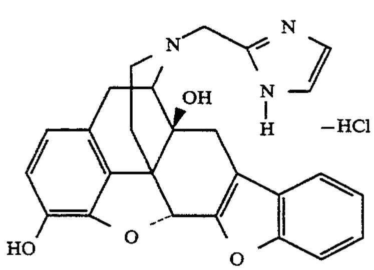 | $C_{26}H_{24}N_3O_4Cl$ + 1.0 H$_2$O + 0.8 HCl | C 59.47<br>H 5.14<br>N 8.00<br>Cl 12.15 | 59.29<br>4.93<br>7.93<br>12.18 | NC |

| Cmpd No. | Structure | Molecular Formula | Microanalysis | | Optical [α]D |
|---|---|---|---|---|---|
| | | | Calcd | Found | |
| 16 | 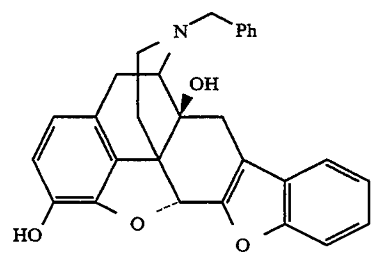 | $C_{29}H_{25}NO_4$ + 0.5 $C_6H_{14}O$ | C 76.47<br>H 6.42<br>N 2.79 | 76.15<br>6.22<br>2.83 | −481.1° |

EXAMPLE I 1,8aβ-Bis(acetyloxy)-5,6,8,8a,9,14bβ-hexahydro-4,8(R,α)-methano-4bS,-7H-bisbenzofuro-[3,2-e:2′,3′-g]isoquinoline-7-carbonitrile (Compound 1)

6,7,8,14bβ-tetrahydro-7-methyl-4,8 (R,α)-methano-4bS*-5H-bisbenzofuro[3,2 e:2′, 3′-g]isoquinoline-1,8aβ(9H)-diol, monohydrochloride (2.50 g, 6.66 mmol) was slurried in a mixture of acetic anhydride (60 mL) and pyridine (30 mL) and stirred for 21 hours at room temperature whereupon a new precipitate formed. The volatiles were removed by rotary evaporation and the residue was taken up into water (100 mL) and extracted with chloroform (2×100 mL). The combined organic extracts were dried (Na2SO4), filtered and evaporated in vacuo to give a residue which was recrystallized from ethyl acetate/chloroform to give 3,14-diacetoxy-6,7,2′,3′-benzofuran-6,7-dehydro-4,5α-epoxy-3,14-dihydroxy-17-methylmorphinan as a white solid. $^1$H NMR (CDCl3) δ7.49 (d, J=8 Hz, 1H), 7.38 (d, J=8 Hz, 1H), 7.29 (t, J=8 Hz, 1H), 7.18 (t, J=8 Hz, 1H), 6.81 (d, J=8 Hz, 1H), 6.68 (d, J=8 Hz, 1H), 5.65 (s, 1H), 4.41 (d, J=7 Hz, 1H), 3.71 (d, J=18 Hz, 1H), 3.30 (d, J=18 Hz, 1H), 2.71 (dd, J=7, 18 Hz, 1H), 2.58–2.45 (comp m, 3H), 2.36 (s, 3H), 2.27 (m, 1H), 2.26 (s, 3H), 1.97 (s, 3H), 1.80 (m, 1H).

The above compound (2.14 g, 4.66 mmol) was dissolved in chloroform (50 mL) and treated with cyanogen bromide (1.97 g, 18.6 mmol). The mixture was heated to reflux for 48 hours before cooling to room temperature. The solution was diluted with chloroform and washed with 1N aqueous hydrochloric acid (50 mL) and water (50 mL), then dried (Na2SO4), filtered and evaporated in vacuo to give a crude residue which was recrystallized from ethyl acetate/hexane to provide the title compound as a white solid. $^1$H NMR (CDCl3) δ7.51 (d, J=8 Hz, 1H), 7.38 (d, J=8 Hz, 1H), 7.33 (t, J=8 Hz, 1H), 7.22 (t, J=8 Hz, 1H), 6.90 (d, J=8 Hz, 1H), 6.76 (d, J=8 Hz, 1H), 5.66 (s, 1H), 5.11 (m, 1H), 3.95 (d, J=18 Hz, 1H), 3.42–3.20 (comp m, 4H), 2.67 (dr, J=7, 14 Hz, 1H), 2.51 (m, 1H), 2.27 (s, 3H), 2.09 (s, 3 H), 1.88 (m, 1H).

EXAMPLE II 6,7,8,14bβ-Tetrahydro-4,8(R,α)-methano-4bS*-5H-bisbenzofuro[3,2-e:2′, 3′-g]isoquinoine-1,8aβ(9H)-dio (Compound 2)

Compound 1 (4.66 mmol) was slurried in a 1:1 mixture of 25% aqueous sodium hydroxide/ethanol and stirred at room temperature until homogeneous. The mixture was then heated at reflux for 70 hours before cooling to room temperature. The mixture was diluted with water (100 mL) and washed with ether (2×100 mL). The aqueous phase was made acidic with 12N hydrochloric acid and then filtered to remove nonbasic solid material. The filtrate was made basic with concentrated aqueous ammonium hydroxide and the resulting solid was filtered, washed with water and dried in vacuo to give the title compound as a tan solid. $^1$H NMR (DMSO d6) δ9.18 (br s, 1H), 7.58 (d, J=8 Hz, 1H), 7.48 (d, J=8 Hz, 1H), 7.32 (t, J=8 Hz, 1H), 7.22 (t, J=8 Hz, 1H), 6.56 (comp m, 2H), 5.53 (s, 1H), 4.8 (brs, 1H), 3.40–2.10 (comp m, 8H), 1.52 (m, 1H).

EXAMPLE III 6,7,8,14bβ-tetrahydro-7-(3-methyl-2-butenyl)-4,8-(R,α)-methano-4bS*-5H-bisbenzofuro[3,2-e:2′,3′-g]-isoquinoline-1aβ(9H) -diol, monohydrochloride (Compound 3)

To a slurry of compound 2 (235 mg, 0.650 mmol) in dimethylformamide (5 mL) was added potassium carbonate (99 mg, 0.71 mmol) and 4-bromo-2-methyl-2-butene (107 mg, 0.72 mmol), and the resulting mixture was heated to 90°–100° C. for 3.5 hours. The mixture was cooled to room temperature and diluted with water (25 mL) before extracting with ethyl acetate (3×25 mL). The combined organic extracts were dried (Na2SO4), then filtered and evaporated in vacuo to give a residue which was purified by silica gel chromatography (eluting with 5% methanol in methylene chloride) to give the free base of compound 3. The free base was taken up in ethanol (ca. 5 mL) and treated with 200 μL of a 7M hydrogen chloride solution in dioxane. The hydrochloride salt was precipitated by the addition of excess ether to give the title compound as a white solid. For the free base of the title compound: $^1$H NMR (CDCl3) δ7.44 (d, J=8 Hz, 1H), 7.38 (d, J=8 Hz, 1H), 7.27 (t, J=8 Hz, 1H), 7.16 (t, J=8 Hz, 1H), 6.65 (d, J=8 Hz, 1H), 6.58 (d, J=8 Hz, 1 H), 5.63 (s, 1H), 5.22 (m, 1H), 4.97 (br s, 2H), 3.23–3.13 (comp m, 2H), 2.84–2.72 (comp m, 3 H), 2.61 (comp m, 2H), 2.32 (m, 2H), 1.83–1.62 (comp m, 2H), 1.78 (s, 3H), 1.69 (S, 3H) .

EXAMPLE IV

Ethyl 5,6,8,8a.9,14bβ-hexahydro-1,8aβ-dihydroxy-4,8(R,α)-methano-4bS*-7H-bisbenzofuro-]3,2-e:2′, 3′-g]isoquinoline-7-acetate hydrochloride (Compound 4)

The title compound was prepared as described in Example III except that ethyl bromoacetate was used in place of the 4-bromo-2-methyl-2-butene. For the free base of the title compound: $^1$H NMR (CDCl$_3$) δ7.43 (d, J=8 Hz, 1H), 7.38 (d, J=8 Hz, 1H), 7.26 (t, J=8 Hz, 1H), 7.16 (t, J=8 Hz, 1H), 6.67 (d, J=8 Hz, 1H), 6.58 (d, J=8 Hz, 1 H), 5.66 (s, 1 H), 4.98 (s, 1 H), 4.76 (s, 1 H), 4.22 (q, J=7 Hz, 2H), 3.38 (ab q, J=17 Hz, 2H), 3.14 (dd, J=6, 12 Hz, 2H), 2.95–2.80 (comp m, 2H), 2.68–2.45 (comp m, 2H), 2.82 (m, 1H), 1.30 (t, J=7 Hz, 3H).

EXAMPLE V 5,6,7.8.8a, 9,14,14bβ-Octahydro-1,8aβ-dihydroxy-7methyl-4,8(R,α) -methano-4bS*-benzofuro[2,3-a]pyrido-[4,3-b]carbazole-11-carboxylic acid, monohydrochloride (Compound 5)

A slurry of oxymorphone hydrochloride (3.00 g, 8.88 mmol) and 4-hydrazinobenzoic acid (1.45 g, 9.50 mmol) in glacial acetic acid (50 mL) was treated with 6N hydrogen chloride in dioxane (1.9 mmol, 11.4 mmol) and then heated to reflux for 5 minutes. The mixture was cooled to room temperature and the resulting brown solid was collected by filtration and washed with ether to provide the title compound as a tan solid after drying under vacuum. $^1$H NMR (CD$_3$OD) δ8.17 (s, 1H) 7.81 (d, J=8 Hz, 1H), 7.38 (d, J=8 Hz, 1H), 6.67 (comp m, 2H), 5.70 (s, 1H), 3.81 (d, J=6 Hz, 1H), 3.51 (d, J=16 Hz, 1H), 3.36–2.68 (comp m, 5}{), 2.98 (S, 3H), 1.93 (m, 1H).

EXAMPLE VI

Ethyl 5,6.7,8,8a,9,14,14bβ-octahydro,8αP-dihydroxy-7-methyl-4,8(R,α)methano-4bS*-benzofuro-[2,3-a]pyrido[4,3-b]carbazole-11-carboxylate, monohydrochloride (Compound 6)

Compound 5 (750 mg, 1.59 mmol) was taken up in ethanol saturated with hydrogen chloride (10 mL) and stirred at room temperature for 48 hours. The volatiles were removed by rotary evaporation and the residue was taken up in water (25 mL). The mixture was made basic with concentrated aqueous ammonium. hydroxide and then extracted with ethyl acetate (3×25 mL). The combined organic extracts were dried (Na$_2$SO$_4$), filtered and evaporated in vacuo to give a residue which was purified by silica gel chromatography (eluting with 7% methanol in methylene chloride) to give the free base of the title compound. The free base was taken up into ethanol, and ethanol saturated with hydrogen chloride was added. The addition of excess ether precipitated a solid which was collected and dried to provide the title compound as a white solid. For the free base of the title compound: $^1$H NMR (CDCl$_3$) δ8.90 (br s, 1H), 7.98 (s, 1H), 7.56 (d, J=8 Hz, 1H), 6.78 (d, J=8 Hz, 1H), 6.55 (d, J=8 Hz, 1H), 6.46 (d, J=8 Hz, 1H), 5.55 (s, 1H), 5.5 (br s, 1H), 4.34 (q, J=7 Hz, 2H), 3.16 (d, J=18 Hz, 1H), 2.97 (d, J=7 Hz, 1H), 2.83–2.70 (comp m, 2H), 2.51 (d, J=16 Hz, 1H), 2.36 (s, 3H), 2.40–2.20 (comp m, 3H), 1.60 (m, 1H), 1.37 (t, J=7 Hz, 3H).

EXAMPLE VII 6,7,8,14bβ-tetrahydro-7-(2,phenylethyl)-4,8(R,α)-methano-4bS*-5H-bisbenzofuro[3,2-e:2', 3'-g]-isoquinoline-1,8aβ(9H)-diol, hydrochloride (Compound 7)

To a slurry of Compound 2 (180 mg, 0.498 mmol) in methanol (5 mL) was added glacial acetic acid (45 mg, 0.75 mmol) and phenylacetaldehyde (72 mg, 0.56 mmol). The mixture was stirred for 10 minutes at room temperature before the addition of sodium cyanoborohydride (63 mg, 1.0 mmol). After stirring for 30 hours, 6N HCl was added (5 mL) and the mixture was stirred an additional 30 minutes before the removal of the solvent by rotary evaporation. The residue was taken up into water (25 mL) and extracted with diethyl ether (2×25 mL). The aqueous phase was made basic with concentrated ammonium hydroxide, and the resulting cloudy mixture was extracted with ethyl acetate (3×25 mL). The combined ethyl acetate extracts were dried (Na$_2$SO$_4$), filtered and evaporated in vacuo to give a residue which was purified by silica gel chromatography (eluting with 5% methanol in methylene chloride) to give the free base of the title compound. The free base was taken up into methanol, and a solution of 7M HCl in dioxane was added (0.2 mL). The addition of excess ether precipitated a solid which was collected and dried to provide the title compound as a white solid. $^1$H NMR (DMSO d-6) δ9.18 (s, 1H), 9.07 (br s, 1H), 7.43 (d, J=7 Hz, 1H), 7.31 (d, J=7 Hz, 1H), 7.22–7.07 (comp m, 7H), 6.48 (m, 2H), 5.59 (s, 1H), 3.89 (br d, J=8 Hz, 1H), 3.41–2.37 (comp m, 11H), 1.67 (m, 1H).

EXAMPLE VIII 5,6,8,8a, 9.14β-Hexahydro-1,8aβ-dihydroxy-4,8-(R,α)-methano-4bS*-7H-bisbenzofuro[3,2-e:2', 3'-g]-isoquinoline-7-acetic acid, hydrochloride (Compound 8)

Compound 4 (124 mg, 0,277 mmol) was taken up into 4N HCl (10 mL) and heated to reflux for 3 hours. The mixture was cooled to room temperature and the solvent was removed by rotary evaporation. The residue was recrystallized from methanol/isopropyl ether to give the title compound as a tan solid. $^1$H NMR (DMSO d-6) δ9.02 (br s, 1H), 7.33 (d, J=7 Hz, 1H), 7.22. (d, J=7 Hz, 1H), 7.08 (t, J=7 Hz, 1H), 6.97 (t, J=7 Hz, 1H) 6.34 (m, 2H), 5.43 (s, 1H), 3.81–2.23 (comp m, 10H), 1.51 (m, 1H).

EXAMPLE IX 6,7,8,8a, 9,14bβ-hexahydro-8aβ-methoxy-7-methyl-4,8(R,α) -methano-4bS*-5H-bisbenzofuro-[3,2 -e: 2',3'-g]isoquinolin-1-ol, monohydrochloride (Compound 9)

Potassium hydride (KH) as a 35% dispersion in oil (275 mg dispersion, 2.40 mmol) was washed via slurrying in pentane (10 mL), followed by the removal of the supernatant oil/pentane from the solid KH. The KH was slurried in THF (15 mL) and cooled to 0° C. and 6,7,8,14bβ-tetrahydro-7-methyl-4,8(R,α)-methano-4bS*-5H-bisbenzofuro[3,2-e:2',3'-g]isoquinoline-1,8aβ(9H)-diol (300 mg, 0.799 mmol) was added. The mixture was warmed to room temperature and stirred for 25 minutes before an addition of iodomethane (580 mg, 4.00 mmol). The resulting cloudy mixture was stirred for 30 minutes before pouring it into 1N HCl (25 mL). The mixture was made basic with concentrated ammonium hydroxide and then extracted with ethyl acetate (3×25 mL). The combined extracts were dried ($Na_2SO_4$), filtered and evaporated in vacuo to give a residue of 3,14-dimethoxy morphinan.

The residue from above was dissolved in methylene chloride (30 mL) and cooled to −78° C. wherein it was treated with boron tribromide (2.04 g, 8.1 mmol). The resulting red solution was allowed to warm to −30° C. and stirred for 45 minutes. The mixture was recooled to −78° C. and treated with methanol (5 mL) and then allowed to warm to room temperature. The solution was poured into 1N HCl (25 mL) and then made basic with concentrated ammonium hydroxide. The mixture was then extracted with methylene chloride (2×25 mL). The combined organic extracts were dried ($Na_2SO_4$), filtered, and evaporated in vacuo to give a residue (320 mg) which was purified by silica gel chromatography (eluting with 5 % methanol in methylene chloride) to give the free base of the title compound. The free base was taken up into methanol and a solution of 7M HCl in dioxane was added (0.15 mL). The addition of excess ether precipitated a solid which was collected and dried to provide the title compound as a white solid. For the free base of the title compound: 1H NMR ($CDCl_3$) δ7.47 (d, J=8 Hz, 1H), 7.38 (d, J−7 Hz, 1H), 7.27 (t, J=7Hz, 1H), 7.19 (t, J=7 Hz,1H), 6.66 (d, J=7Hz, 1H), 6.57 (d, J=7Hz, 1H), 5.63 (s, 1H), 3.39–3.29 (comp m, 2H), 3.25 (s, 3H), 3.02 (d, J=16 Hz, 1H), 2.60 comp m, 3H), 2.43 (s, 3H), 2.33 (d, J=16 Hz, 1H), 2.28 (m, 1H), 1.68 (dd, J=4, 11 Hz, 1H).

EXAMPLE X 6,7,8,8a,9,14bβ-hexahydro-7-methyl-8aβ-(phenylmethoxy)-4,8(R,α)-methano-4bS*
-5H-bisbenzofuro[3,2-e:2′,3′-g]isoquinolin-1-ol, monohydrochloride (Compound 10)

Sodium hydride, as a 60% dispersion in oil (112 mg dispersion, 2.80 mmol) was washed with pentane (5 mL) to remove the oil and then suspended in dimethylformamide (DMF, 20 mL) and cooled in an ice bath. 6,7,8,14bβ-tetrahydro-7-methyl-4,S(R,α)-methano-4bS,-5H-bisbenzofuro[3,2-e:2′, 3′, -g]isoquinoline-1,8aβ(9H)-diol (1.00 g, 2.66 mmol) was added in one portion and the mixture was stirred for.20 minutes before an addition of iodomethane (772 mg, 5.33 mmol). The mixture was stirred for 15 minutes at 0° C. and 45 minutes at room temperature and then poured into 0.5N aqueous HCl (50 mL). The mixture was extracted with diethyl ether (50 mL) and the aqueous phase was made basic with concentrated aqueous ammonium hydroxide. The cloudy solution was extracted with ethyl acetate (3×50 mL) and the combined organic extracts were washed with water (2×50 mL), then dried ($Na_2SO_4$), filtered and evaporated in vacuo to give the crude product. The product was purified by silica gel chromatography, eluting with 5% methanol in methylene chloride to give the 3-methoxy derivative.

Potassium hydride (KH) as a 35% dispersion in oil (148 mg dispersion, 1.29 mmol) was washed via slurrying in pentane (5 mL), followed by the removal of the supernatant oil/pentane from the solid KH. The 3-methoxy derivative (335 mg, 0.800 mmol) was added as a solution in 5 mL DMF to the KH and stirred for 20 minutes before an addition of benzyl bromide (294 mg, 1.72 mmol). After stirring for 44 hours, the mixture was poured into 1N aqueous HCl (25 mL) and extracted with diethyl ether (25 mL). The aqueous phase was made basic with concentrated aqueous ammonium hydroxide and then extracted with ethyl acetate (2×25 mL). The combined ethyl acetate extracts were dried ($Na_2SO_4$), filtered, then evaporated in vacuo to give a residue which was purified by silica gel chromatography, eluting with 2% methanol in methylene chloride to give the 3-methoxy-14-benzyloxy intermediate.

Sodium hydride, as a 60% dispersion in oil (163 mg dispersion, 4.06 mmol) was washed with hexane (5 mL) to remove the oil and then suspended in dimethylformamide (DMF, 2 mL). Ethanethiol (202 mg, 3.25 mmol) was added and the mixture was stirred for 20 minutes whereupon a yellow precipitate formed. The 3-methoxy-14-benzyloxy compound (78 mg, 0.16 mmol) was added as a solution in 4 mL DMF and the mixture was heated to 125°–135° C. for 4 hours. The mixture was cooled to room temperature and poured into 1N aqueous HCl (25 mL). The mixture was extracted with diethyl ether (2×25 mL) to remove neutral organics and then made basic with concentrated aqueous ammonium hydroxide. The mixture was extracted with ethyl acetate (2×25 mL), and the combined ethyl acetate extracts were dried ($Na_2SO_4$), filtered, then evaporated in vacuo. The resulting residue was purified by silica gel chromatography, eluting with 5% methanol in methylene chloride to give the free base of the title compound. The free base was taken up into methanol and a solution of 7M HCl in dioxane was added (0.15 mL). The addition of excess ether precipitated a solid which was collected and dried to provide the title compound as a white solid. For the free base of the title compound: 1H NMR ($CDCl_3$) δ7.42 (d, J=7 Hz, 1H), 7.28 (d, J=7 Hz, 11{), 7.23 (t, J=7 1{z, 1H), 7.17–7.09 (comp m, 6H), 6.65 (d, J=7 Hz, 1H), 6.56 (d, J=7 Hz, 1H), 5.64 (s, 11{), 4.73 (d, J=11 Hz, 1H), 4.40 (d, J=11 1 Hz, 1H), 3.50 (d, J=6 Hz 1H) 3.34 (d, J=18 Hz 1H, ), 3.02 (d, J=16 Hz, 1H), 2.77–2.55 (comp m, 3H), 2.42 (s, 31H), 2.36–2.27 (comp m, 2H), 1.68 (m, 1H).

EXAMPLE XI 5.6.7,8,8a,9,14,14bβ-octahydro-1,8aβ-dihydroxy-7-methyl-4,(R,α)-methano-7-(2-propenyl]-4bS*-benzofuro-[2,3-a]pyrido[4,3-b]carbazole-11-carboxvlic acid, hydrochloride (Compound 11)

The title compound was prepared as described in Example V except that naloxone hydrochloride dihydrate was used in place of the oxymorphone hydrochloride. 1H NMR ($CD_3OD$) δ8.18 (s, 1H), 7.81 (d, J=8 Hz, 1H), 7.37 (d, J=8 Hz, 1H), 6.67 (comp m, 2H), 5.98 (m, 1H), 5.69 (s, 1H), 5.73–5.64 (comp m, 2H), 3.86–2.64 (10H), 1.93 (m, 1H).

EXAMPLE XII 5,6,7,8,14,14bβ-Hexahydro-13-iodo-7- methyl-4,8-(R,60 )-methano-4bS*-benzofuro[2,3-a]pyrido[4,3-b]-carbazole-1,8aβ(9H]-diol, monohydrochloride (Compound 12)

The title compound was prepared as described in Example V except that 2-iodophenyl hydrazine was used in place of the 4-hydrazinobenzoic acid. 1H NMR (CD₃OD) δ7.53 (d, J=8 Hz, 1H), 7.41 (d, J=8 Hz, 1H), 6.77 (t, J=8 Hz, 1H), 6.68 (comp m, 2H), 5.76 (s, 1H), 3.81 (d, J=7 Hz, 1H), 3.51 (d, J=16 Hz, 1H), 3.38–3.18 (4H), 2.967 (s, 3H), 2.72 (comp m, 2H), 1.95 (m, 1H).

EXAMPLE XIII
5,6,7,8,14,14bβ-Hexahydro-7-[[5-(hydroxymethyl)-2-furanyl]methyl]-4,8(R,α),methano-4bS*-benzofuro[2,3-a]pyrido[4,3-b]carbazole-1,8aβ(9H]-diol, monohydrochloride (Compound 13)

The title compound was prepared by the method described in Example VII except that 5-(hydroxymethyl)furfural was used in place of the phenylacetaldehyde. ¹H NMR (CD₃OD) δ7.48 (d, J=8 Hz, 1H), 7.41 (d, J=8 Hz, 1H), 7.31 (t, J=8 Hz, 1H), 7.20 (t, J=8 Hz, 1H), 6.72 (comp m, 3H), 6.46 (d, J=3Hz, 1H), 5.68 (s, 1H), 4.61 (s, 2H), 4.42 (m, 1H), 3.70–2.60(9H), 2.00 (m, 1H).

EXAMPLE XIV
7-(3-Furanylmethyl)-5.6.7,8,14,14bβ-hexahydro-4,8 (R,α) -methano-4bS*-benzofuro[2,3-a]pyrido-[4,3-b]carbazole-1,8aβ(9H) -diol, hydrochloride (Compound 14 )

The title compound was prepared by the method described in Example VII except that 3-furaldehyde was used in place of the phenylacetaldehyde. ¹H NMR (CD₃OD) δ7.88 (s, 1H), 7.72 (s, 1H), 7.46 (d, J=8 Hz, 1H), 7.41 (d, J=8 Hz, 1H), 7.32 (t, J=8 Hz, 1H), 7.21 (t, J=8 Hz, 1H), 6.73 (comp m, 3H), 5.70 (s, 1H), 4.50 (d, J=15 Hz, 1H), 4.28 (d, 15 Hz, 1H), 3.60–2.60 (8H) 2.08 (m, 1H).

EXAMPLE XV
5.6,7,8,14.14bβ-Hexahydro-(1H-imidazol-2-ylmethyl)-4,8(R,α) -methano-4bS*-benzofuro [2,3-a]pyrido-[4.3-b]carbazole-1.8aβ(9H) -diol, hydrochloride (Compound 15)

The title compound was prepared by the method described in Example VII except that 2-imidazolecarboxaldehyde was used in place of the phenylacetaldehyde. ¹H NMR (CD₃OD) δ7.65 (s, 2H), 7.47 (comp m, 2H), 7.30 (t, J=8 Hz, 1H), 7.20 (t, J=8 Hz, 1H), 6.68 (comp m, 3H), 5.65 (s, 1H), 4.52 (comp m, 2H), 3.55–2.60 (8H), 1.90 (m, 1H).

EXAMPLE XVI
6,7,8,14bβ-Tetrahydro-7-(2-phenylmethyl)-4,8-(R,α)-methano-4bS*-5H-bisbenzofuro-[3,2-e:2',3'-g]isoquinoline-1,8aβ(9H)-diol (Compound 16)

6,7,8,14bβ-Tetrahydro-4,8(R,α)-methano-4bS,-5H-bisbenzofuro[3,2-e:2',3'-g]isoquinoline-1,8aβ(9H)-diol (125 mg, 0,346 mmol) was slurried in dimethylformamide (3 mL). Potassium carbonate (53 mg, 0.38 mmol) and benzyl bromide (65 mg, 0.38 mmol) were added and the resulting mixture was heated to 90°–100° C. for 3 hours. The mixture was cooled to room temperature and diluted with water (25 mL) before extracting with chloroform (2×25 mL). The combined organic extracts were evaporated in vacuo to give a residue which was purified by silica gel chromatography, eluting with 10% methanol in methylene chloride. The product was recrystallized from isopropyl ether/hexane to give the title compound as a white solid. ¹H NMR (CDC₃)δ7.45 (d, J=8 Hz, 1H), 7.39–7.24 (comp m, 7H), 7.16 (t, J=8 HZ, 1H), 6.67 (d, J=8 Hz, 1H), 6.61 (d, J=8 Hz, 1H), 5.63 (s, 1H), 4.87 (br s, 1H), 4.69 (br s, 1H), 3.71 (br s, 2H), 3.32 (d J=18 Hz, 1H), 3.12 (d, J=7 Hz, 1H), 2.96–2.37 (comp m, 6H), 1.72 (d, J=10 HZ, 1H).

(6) Description of the Assays

The biological activities of the compounds of this invention were determined by the following test procedures.

(a) Writhing Assay

The Writhing Assay is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., Arch. int. Pharmacodyn, 267, 131–140 (1984); C. Vander Wende et al., Fed. Proc., 15, 494 (1956); Koster et al., Fed. Proc., 18, 412 (1959); and Witken et al., J. Pharmacol. exp. Ther., 133, 400–408 (1961).] Chemicals which may be used to induce this pain include phenylbenzoquinone (PBQ) and acetic acid. As a result of the chemical irritation to the animal, a characteristic stretching and writhing of the animal (dorsiflexion of the animal's back, extension of its hind-limbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds of the present invention exhibit analgesic activity in mice, as shown by the results of the Writhing Assay presented in Table I below.

Charles River male albino mice, weighing 20 to 30 grams were used in this assay.

Thirty minutes after subcutaneous or intragastric administration to ten mice of either 10 mg or 30 mg per kilogram of body weight of a compound of the present invention ("test compound"), 0.1 mg per 10 g of body weight of a 0.025% w/v solution of PBQ was injected intraperitoneally into each mouse. Ten mice which were given saline in place of a test compound of the invention were used as a control group.

Five minutes later, each mouse was individually placed into a glass beaker for observation, and the number of writhes occurring during the following ten minute period was counted.

A test compound was considered to have produced analgesia in a mouse if, in accordance with the conditions set forth above, and under the test criteria employed for this assay, after the administration of 10 or 30 mg per kilogram of body weight of a compound of the present invention to the mouse, the number of writhes elicited by a mouse injected with PBQ was equal to, or less than, one-half the median number of writhes recorded for the saline-treated control group of mice that day, as described by Taber in "Predictive Value of Analgesic Assays in Mice and Rats," Advances in Biochemical Psychopharmacology, 8, 191 (1974).

The results for the particular compounds of the present invention analyzed in this assay, and discussed in the examples identified below which correspond thereto, are presented in Table I hereinbelow as fractions under the heading "PBQ Writhing Assay." The fractions indicate the number of mice, out of ten, in which the test compound produced analgesia in accordance with the conditions set forth above, and under the test criteria employed for this assay.

The standard initial screening doses of a test compound employed in this assay were 10 and/or 30 mpk per gram of body weight for both routes of administration. If the initial screening dose of the compound produced analgesia in seven of ten mice, then the effect of additional doses of the compound on the writhing response was evaluated, and then the $ED_{50}$ dose was generally calculated. (The slopes of the dose-response curves for the compounds analyzed were compared as described by Tallarida and Murray, *Manual of Pharmacologic Calculations*, Page 11 (Springer Verlag, N.Y., 1981)).

All $ED_{50}$ doses calculated are also presented below as whole numbers in Table I under the headling "PBQ WRITHING ASSAY." As Table I shows, the most potent compound of the present invention tested in the Writhing Assay was the compound shown and discussed in Example V.

TABLE I

| Data Generated from the Writhing Assay PBO WRITHING ASSAY | | |
|---|---|---|
| | ($ED_{50}$ {mpk}) | |
| EXAMPLE NUMBER | I.G. | S.C. |
| I | inactive at the initial screening dose | 2.4 |
| II | 4/10* | 4/10* |
| V | 3.4 | 1.3 |

*Number of mice in 10 exhibiting inhibition of writhing (b) Tail Flick Assay

The "Tail Flick Assay" uses thermal pain of transient duration, and is a test in which the pain threshold of the mice or rats being analyzed has not been altered. It is useful for evaluating the ability of a compound or drug to increase the animal's pain threshold (i.e. prolong response latencies), rather than to restore normal thresholds.

The heat-induced response to the Tail Flick Assay is a reflex reaction mediated at the level of the spinal cord.

Opiate compounds having clinical efficacy as analgesics generally increase tail flick latencies. Thus, morphine and codeine are generally determined to be active in this test. In contrast, aspirin and Zomax, which are Non-Steroidal Antiinflammatory Drugs (NSAIDs), show little activity in this test.

The Tail Flick Assay was performed generally in the manner described by G. Woolfe et al., "The Evaluation of the Analgesic Action of Pethidine Hydrochloride (Demerol)," *J. Pharmacol. Exp. Ther.*, 80, 300, (1944), F. D'Amour et al., "A Method for Determining Loss of Pain Sensation, " *J. Pharmacol. Exp . Ther.*, 72, 74, 300–307 (1941), and E. Drower et al., "The Antinociceptive Effects of Prostaglandin Antagonists in the Rat," *European Journal of Pharmacology*, 133, 249–256 (1987).

Male Charles River albino mice, and male Charles River Sprague-Dawley rats, weighing 20 to 30 g, and 200 to 250 g, respectively, were employed in this assay.

Tail flick response latencies (defined as the time that elapsed between the onset of a high intensity beam of light and the reflex removal of the mouse or rat's tail) was measured before (baseline) and again at fixed intervals after subcutaneous or intracerebroventricular administration of one of the compounds of the invention, or after the administration of saline (controls). The cut-off latencies established to prevent tissue damage in the animals are 12 seconds or 14 seconds in the mouse and rat, respectively, in the Tail Flick Assay. The significance of any increase in tail flick response latency is determined using analyses of variance.

One way analyses of variance were used to determine the significance of the effect of the compounds of the invention on response latencies. For this assay, the $ED_{50}$ value was defined as the dose of a compound which produced one half the maximum possible increase in latency (i.e., to 7.5 and 8.5 seconds in the mouse and rat, respectively). Calculations of $ED_{50}$ values were based upon a least squared linear regression equation computed for the data at a time of peak effect, as described by D'Amour and Woolfe, supra.

"Activity" or "Inactivity" was determined at a particular concentration of the compound by a significant increase in tail flick latency above normal latencies.

The data resulting from the Tail Flick Assay are presented in Table II below.

TABLE II

| Data Generated from the Tail Flick Assay | | |
|---|---|---|
| Compound Tested Example Number | Subcutaneous (S.C.) | Intracerebroventricular I.G. |
| IX | active at >30 mpk | 10.5 nmoles |
| XV | inactive | ~10 nmoles |

The data presented in Table II show that, when administered intracerebroventricularly, the compounds of examples IX and XV are active at a dose of ca. 10 nmoles.

(3) Opiate Binding Assay

Compounds within the present invention were also evaluated in an opioid radioligand binding assay, which measures the affinity of opioids for specific opioid receptors in rat forebrain, by their ability to displace the binding of radiolabeled ligands specifically bound to μ and/or δ opioid receptors isolated from rat brain. Compounds which are determined to be active in this in vitro assay will generally have opioid-like effects in animals, including analgesia, unless they are not bioavailable.

A purified homogenate of receptor membranes was prepared from the brains. of the rats according to the method described by K. J. Chang et al., "Multiple Opiate Receptors: Enkephalins and Morphine Bind to Receptors of Different Specitivity, " *J. Biol Chem.*, 254, 2610–2618 (1979).

Male Charles River Sprague-Dawley albino rats weighing 150 to 300 g were stunned and decapitated. Their forebrains (minus the cerebellum and associated hindbrain) were quickly removed and rinsed in ice-cold 50 mM Tris buffer, pH 7.4, and homogenized in 20 volumes of buffer with a Polytron (Brinkman) at setting 6 for 30 seconds. The membranes were washed by centrifugation for 20 minutes at $30,000 \times g$, followed by resuspension to twice the original volume. The homogenate was incubated at 25° for 1 hour, followed by centrifugation as above.

The resulting homogenate was then assayed for protein content according to the method described by Itzhaki et al., "A Micro-Biuret Method for Estimating Proteins," *Anal Biochem.*, 9, 401–410 (1961). The . final pellet was resuspended to a protein concentration of 10 mg protein per mL (assuming 6% of wet weight is protein) and 4 mL aliquots were rapidly frozen in liquid $N_2$.

The binding of compounds within the invention to the rat brain opiate receptor membrane preparation containing either δ or μ opioid receptors was measured using a modification of the method of C. B. Pert et al., "Properties of Opiate Receptor Binding in Rat Brain," *Proc. Natl. Acad. Sci.*, 70, 2243–2247 (1972).

The opiate binding assays were conducted in triplicate at 37° C. in 50 mM Tris HCl buffer at pH 7.4 in a final volume of 1 mL, using varying concentrations of a compound of the invention. Each of three tubes contained 0.8 mL of homogenate containing approximately 1 mg/mL of protein. $^3$[H]-DAMGO (2.0 nM) and $^3$[H]-DSLET (1.0 nM) were used to label the μ and δ opiate rat brain receptors, respectively.

The "percent displacement" of radiolabeled ligand ($^3$[H]-DAMGO for the μ receptors and $^3$[H]-DSLET for the δ receptors) bound to the μ or δ opioid receptors by a compound of the present invention was determined at different concentrations of the compound (10μM, 1μM, 100 nM and/or 1 nM). Because the radiolabeled ligand and the compound compete with each other for the opiate receptor binding sites, the greater the percent of displacement of the bound radiolabeled ligand, the better the compound is in terms of its ability to bind to the opiate receptors and, thus, the more potent the compound is. "Specific binding" of a compound of the present invention to the μ or the δ opiate rat brain receptors was defined as the difference between total binding and that in the presence of 10 μM of levorphanol.

For those compounds which bound particularly well to the opiate receptors, the mean $IC_{50}$ value (that concentration of a particular compound which is required to have 50 percent of the bound radiolabeled ligand displaced from the opiate receptors) was calculated (nM). $IC_{50}$ values were determined from log-logit plots of concentration vs. time response curves. Comparison of $IC_{50}$ values in this assay system provides a measure of the receptor specificity of the tested compounds.

Finally, for those compound for which a mean $IC_{50}$ value was calculated for both the μ and δ opioid receptors, the ratio of the mean $IC_{50}$ values for the μ and δ opioid receptors was determined. This ratio indicates how specific a particular compound is for the δ opioid receptors. Thus, if the ratio of the mean $IC_{50}$ values is 1.0, the compound is approximately equally specific for both the μ and the δ opioid receptors. The greater the number is above 1.0, the more specific the compound is for the δ opioid receptors.

The results obtained from this opiate binding assay are shown in Table III below, and correspond to the compound shown and described in the particular example identified below which corresponds thereto.

TABLE III

| Data Obtained from the Opiate Binding Assay | | | | |
|---|---|---|---|---|
| Example Number | | Per Cent Displacement | Mean $IC_{50}$ Value | Mean $IC_{50}$ μ/δ Ratio |
| Example I | (δ) | 14% at 100 nM | | |
| Example II | (μ) | 2 | 291 | 45 |
|  | (δ) |  | 6.5 | 45 |
| Example III | (μ) |  | 4670 | 91 |
|  | (δ) |  | 51.1 | 91 |
| Example IV | (μ) |  | >10000 | >850 |
|  | (δ) |  | 11.8 | >850 |
| Example V | (μ) |  | 810 | 1.2 |
|  | (δ) |  | 660 | 1.2 |
| Example VI | (μ) |  | 248 | 3.8 |
|  | (δ) |  | 65 | 3.8 |
| Example VII | (μ) | 35% at 1 μM | N C | — |
|  | (δ) |  | 34.5 | — |
| Example VIII | (μ) |  | 4000 | 25 |
|  | (δ) |  | 160 | 25 |
| Example IX | (μ) |  | 430 | 430 |
|  | (δ) |  | 1 | 430 |
| Example X | (μ) |  | 356 | 44 |
|  | (δ) |  | 8 | 44 |
| Example XII | (μ) |  | 101 | 10.6 |
|  | (δ) |  | 9.5 | 10.6 |
| Example XIII | (μ) |  | inactive | — |
|  | (δ) |  | ~100 | — |
| Example XIV | (μ) |  | inactive | — |
|  | (δ) |  | 31.8 | — |
| Example XV | (μ) |  | inactive | — |
|  | (δ) |  | 79.2 | — |
| Example XVI | (μ) |  | inactive | — |
|  | (δ) |  | 50% at 50 nM | — |

— = Not Applicable (Because the Mean $IC_{50}$ Value was not Calculated)
NC = Not calculated (7) Dosage and Mode of Administration The compounds of the present invention, and the pharmaceutical compositions comprising one or more of these compounds in combination with a pharmaceutically-acceptable carrier, are useful in treating pain in animals. A physician or veterinarian of ordinary skill in the art can readily determine whether or not a particular patient is in pain.

The pharmaceutical compositions of the present invention, which will typically comprise one or more of the compounds of Formula I as an active ingredient in admixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration. They may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are orally and parenterally, the most preferred mode of administration is orally.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the present invention will be that amount of the compound which is the lowest dose effective to produce a therapeutic effect. Such an effective dose will generally depend upon the factors described above. Generally, dosage levels in the range of from about 0.001 mg to about 10 g, more preferably from about 1 mg to about 1000 mg, of active compound (a compound of Formula I) per kilogram of body weight per day are administered to a mammalian patient. However, the total daily usage of the compounds of Formula I, or the pharmaceutical compositions comprising such compounds, will be determined by an attending physician or veterinarian within the scope of sound medical judgement.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically-acceptable antioxidants include: (1) water soluble antioxidants, such as ascorbic acid, cysteine hydrochloride, sodium bisulfite, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which is the lowest dose effective to produce a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile, injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically-acceptable emulsions, microemulsions, solutions, suspensions, syrups and elixirs. In addition to the active ingredient (compound of Formula I), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, wheat germ, olive, and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving, dispersing or otherwise incorporating a compound of the present invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Opthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable dosage forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable media just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

What is claimed is:

1. A compound of the formula:

[structure]

or a pharmaceutically-acceptable salt thereof, wherein:

$R^1$ is hydrogen, $C_1$-$C_6$ alkyl, $C_3$-$C_6$ alkenyl, aryl, —CN, $$-(CH_2)_n-\overset{O}{\underset{\|}{C}}-OR$$

or —A–B, wherein n is an integer of from 1 to 5, and wherein A is alkylene having one or two carbon atoms and B is aryl or arylalkylhydroxy;

R is —H or —$C_1$-$C_5$ alkyl;

$R^2$ is —OH, —O-$C_1$-$C_5$ alkyl, $$-O-\overset{O}{\underset{\|}{C}}-C_1-C_5$$

alkyl or —O-alkylaryl;

$R^3$ is hydrogen, $C_1$-$C_6$ alkyl, $$-\overset{O}{\underset{\|}{C}}-H, \quad -\overset{O}{\underset{\|}{C}}-C_1-C_5 \text{ alkyl or } -\overset{O}{\underset{\|}{C}}-C_1-C_5 \text{ alkoxy;}$$

X is —$NR^6$ or O;

$R^6$ is hydrogen or $C_1$-$C_6$ alkyl; and

Y is hydrogen, $$-\overset{O}{\underset{\|}{C}}-OR$$

or I.

2. A compound of claim 1 wherein $R^1$ is hydrogen, —CN, $C_1$-$C_6$ alkyl, $C_3$-$C_6$ alkenyl, —A–B or $$-(CH_2)_n-\overset{O}{\underset{\|}{C}}-OR.$$

3. A compound of claim 2 wherein X is O or —NH.

4. A pharmaceutical composition comprising a pharmaceutically acceptable carrier and a therapeutically-effective amount of a compound of the formula:

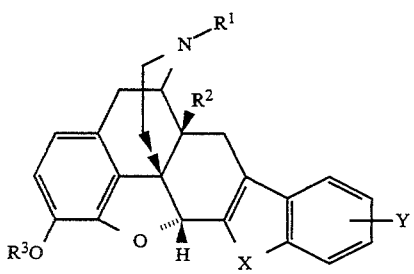

or a pharmaceutically-acceptable salt thereof, wherein:
$R^1$ is hydrogen, $C_1-C_6$ alkyl, $C_3-C_6$ alkenyl, aryl, —CN,

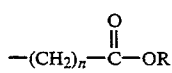

or —A–B, wherein n is an integer of from 1 to 5, and wherein A is alkylene having one or two carbon atoms and B is aryl or arylalkylhydroxy;
R is —H or —$C_1-C_5$ alkyl;
$R^2$ is —OH, —O-$C_1-C_5$ alkyl,

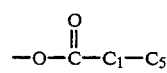

alkyl or —O-alkylaryl;
$R^3$ is hydrogen, $C_1-C_6$ alkyl,

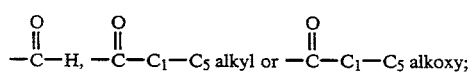

X is —$NR^6$ or O;
$R^6$ is hydrogen or $C_1-C_6$ alkyl; and
Y is hydrogen,

or I.

5. The pharmaceutical composition of claim 4 wherein $R^1$ is hydrogen, —CN, $C_1-C_6$ alkyl, $C_3-C_6$ alkenyl, —A–B or

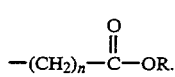

6. The pharmaceutical composition of claim 4 wherein $R^1$ is hydrogen, $C_1-C_6$ alkyl, $C_3-C_6$ alkenyl, —CN, —A–B or

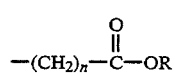

and X is —NH or O—.

7. A method of treating analgesia in an animal comprising administering to the animal a compound of the formula:

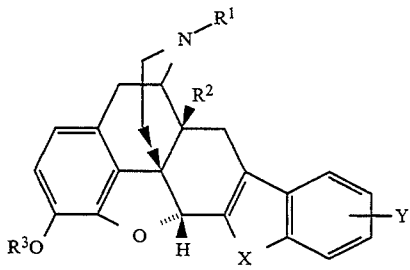

or a pharmaceutically-acceptable salt thereof, wherein:
$R^1$ is hydrogen, $C_1-C_6$ alkyl, $C_3-C_6$ alkenyl, aryl, —CN,

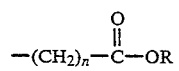

or —A–B, wherein n is an integer of from 1 to 5, and wherein A is alkylene having one or two carbon atoms and B is aryl or arylalkylhydroxy;
R is —H or —$C_1-C_5$ alkyl;
$R^2$ is —OH, —O-$C_1-C_5$ alkyl,

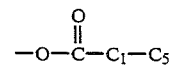

alkyl or —O—alkylaryl;
$R^3$ is hydrogen, $C_1-C_6$ alkyl,

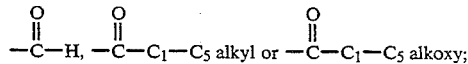

X is —$NR^6$ or O;
$R^6$ is hydrogen or $C_1-C_6$ alkyl; and
Y is hydrogen,

or I.

8. The method of claim 8 wherein $R^1$ is hydrogen, —CN, $C_1-C_6$ alkyl, $C_3-C_6$ alkenyl, —A–B or

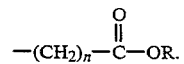

9. The method of claim 8 wherein X is —NH or O.
10. A compound of the formula:

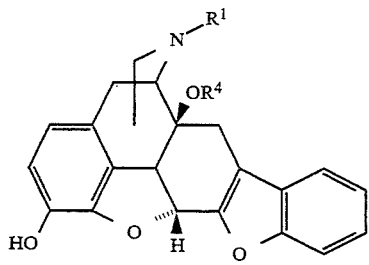

or a pharmaceutically-acceptable salt thereof, wherein:
$R^1$ is $C_1-C_6$ alkyl; and
$R^4$ is alkylaryl.

* * * * *

UNITED STATES PATENT AND TRADEMARK OFFICE
CERTIFICATE OF CORRECTION

PATENT NO. : 5,436,249
DATED : July 25, 1995
INVENTOR(S) : Dappen, et al.

It is certified that error appears in the above-indentified patent and that said Letters Patent is hereby corrected as shown below:

Title page abstract, that part of the formula reading

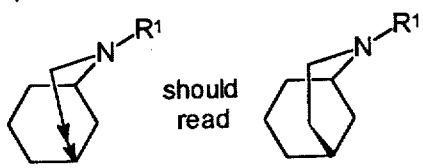

Column 2, line 35, Column 36, line 5, Column 37, line 1 and Column 38, line 1, that part of the formula reading

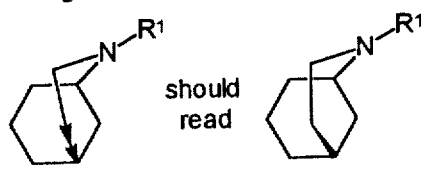

Column 7, line 1, reading "acceptable-salts" should read --acceptable salts--.

Column 7, line 37, reading "Salts,." *J Pharm Sci.,*" should read --Salts," *J.Pharm.Sci.,*--.

Column 8, line 54, reading "-CH," should read -- -CN, --.

Columns 14, 16, 18 and 20 in Table Header reading "Optical $[\alpha]_D$" should read --Optical Rotation $[\alpha]_D$--.

Column 19, line 19, reading "4bS,-" should read --4bS*---.
Column 19, line 58, reading "(dr, J" should read --(dt, J--.
Column 19, line 63, reading "dio" should read --diol--.

UNITED STATES PATENT AND TRADEMARK OFFICE
CERTIFICATE OF CORRECTION

PATENT NO. : 5,436,249
DATED : July 25, 1995
INVENTOR(S) : Dappen, et al.

Page 2 of 4

It is certified that error appears in the above-indentified patent and that said Letters Patent is hereby corrected as shown below:

Column 21, line 14, reading "-7methyl" should read ---7-methyl--.

Column 21, line 33, reading "(comp m, 5}-{)," should read --(comp m, 5H),--.

Column 21, line 33, reading "2.98(S,3H)" should read --2.98(s,3H)--.

Column 21, line 39, reading "octahydro" should read --Octahydro--.

Column 21, line 49, reading "ammonium.hydroxide" should read --ammonium hydroxide--.

Column 22, line 3, reading "(2,phenylethyl)" should read --(2-phenylethyl)--.

Column 22, line 38, reading "9.14β" should read --9,14β--.

Column 22, line 43, reading "0,277" should read --0.277--.

Column 22, line 49, reading "7.22." should read --7.22--.

Column 23, line 29, reading "Hz, IH" should read --Hz, 1H--.

Column 23, line 41, reading "Compound 10)" should read --(Compound 10)--.

Column 23, line 46, reading "4,S" should read --4,8--.

Column 23, line 47, reading "4bS," should read --4bS*--.

UNITED STATES PATENT AND TRADEMARK OFFICE
CERTIFICATE OF CORRECTION

PATENT NO. : 5,436,249
DATED : July 25, 1995
INVENTOR(S) : Dappen, et al.

It is certified that error appears in the above-indentified patent and that said Letters Patent is hereby corrected as shown below:

Column 23, line 49, reading "for.20" should read --for 20--.
Column 24, line 38, reading "11{)" should read --1H)--.
Column 24, line 38, reading "1{z," should read --1Hz,--.
Column 24, line 40, reading "11{)" should read --1H)--.
Column 24, line 40, reading "(d, J = $^{111Hz}$," should read --(d, J = 11Hz,--.
Column 24, line 41, reading "6 Hz1H)" should read --6 Hz,1H)--.
Column 24, line 41, reading "18 Hz1H)" should read --18 Hz,1H)--.
Column 24, line 42, reading "(s, 31H)" should read --(s, 3H)--.
Column 24, line 46, reading "(5.6." should read --5,6,--.
Column 24, line 46, reading "octahydro" should read --Octahydro--.
Column 24, line 48, reading "carboxvlic" should read --carboxylic--.
Column 24, line 62, reading "(R, 60)" should read --(R, α)--.
Column 24, line 63, reading "(9H]" should read --(9H)--.
Column 25, line 8, reading "(9H]" should read --(9H)--.
Column 25, line 22, reading "5.6." should read --5,6,--.
Column 25, line 32, reading "(8H)" should read --(8H),--.
Column 25, line 36, reading "5.6,7,8,14." should read --5,6,7,8,14--.
Column 25, line 38, reading "[4.3" should read --[4,3--.
Column 25, line 38, reading "1.8αβ" should read --1,8αβ--.

UNITED STATES PATENT AND TRADEMARK OFFICE
CERTIFICATE OF CORRECTION

PATENT NO. : 5,436,249
DATED : July 25, 1995
INVENTOR(S) : Dappen, et al.

It is certified that error appears in the above-indentified patent and that said Letters Patent is hereby corrected as shown below:

Column 25, line 58, reading "0,346 mmol)" should read --0.346 mmol)--.

Column 26, line 1, reading "(CDC$_3$)" should read --(CDCl$_3$)--.

Column 26, line 3, reading "8 HZ,1H)" should read --8 Hz,1H)--.

Column 26, line 6, reading "10 HZ,1H)" should read --10Hz,1H)--.

Column 27, line 18, reading "headling" should read --heading--.

Column 28, line 47, reading "brains." should read --brains--.

Column 28, line 66, reading "Anal Biochem.," should read --Anal. Biochem.,--.

Column 28, line 66, reading "The." should read --The--.

Column 29, line 10, reading "Tris HCl" should read --Tris/HCl--.

Column 38, line 55, that part of the formula reading

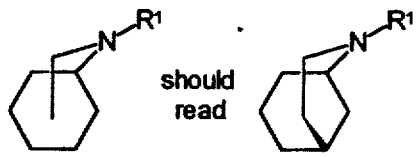 should read 

Signed and Sealed this

Fifteenth Day of July, 1997

Attest:

BRUCE LEHMAN

Attesting Officer

Commissioner of Patents and Trademarks